United States Patent
Yamazaki et al.

(10) Patent No.: US 10,408,787 B2
(45) Date of Patent: Sep. 10, 2019

(54) ELECTROPHORESIS APPARATUS, CAPILLARY ARRAY, AND CAPILLARY UNIT

(75) Inventors: Motohiro Yamazaki, Mito (JP);
Michiru Fujioka, Hitachinaka (JP);
Takamichi Muramatsu, Tokyo (JP);
Takashi Gomi, Hitachinaka (JP)

(73) Assignee: HITACHI HIGH-TECHNOLOGIES CORPORATION, Tokyo (JP)

( * ) Notice: Subject to any disclaimer, the term of this patent is extended or adjusted under 35 U.S.C. 154(b) by 852 days.

(21) Appl. No.: 13/976,157

(22) PCT Filed: Nov. 30, 2011

(86) PCT No.: PCT/JP2011/006674
§ 371 (c)(1),
(2), (4) Date: Jul. 17, 2013

(87) PCT Pub. No.: WO2012/101705
PCT Pub. Date: Aug. 2, 2012

(65) Prior Publication Data
US 2013/0292251 A1 Nov. 7, 2013

(30) Foreign Application Priority Data
Jan. 26, 2011 (JP) .................................. 2011-013566

(51) Int. Cl.
*G01N 27/447* (2006.01)
*G01N 30/60* (2006.01)

(52) U.S. Cl.
CPC . *G01N 27/44704* (2013.01); *G01N 27/44721* (2013.01); *G01N 27/44782* (2013.01); *G01N 30/6091* (2013.01)

(58) Field of Classification Search
CPC ................. G01N 27/447; G01N 27/26; G01N 27/44769; B01L 2400/0415; B01L 2400/0421; B01L 3/502753; C07K 1/26
(Continued)

(56) References Cited

U.S. PATENT DOCUMENTS 4,364,670 A * 12/1982 White ..................... G04G 9/06
204/600
4,466,878 A * 8/1984 DiNitto ................ G01N 27/404
204/415

(Continued)

FOREIGN PATENT DOCUMENTS

CN          1922479 A     2/2007
EP        1 378 745 A1    1/2004

(Continued)

OTHER PUBLICATIONS

CN Office Action for Chinese Application No. 201180065985.0, dated May 5, 2014.

(Continued)

*Primary Examiner* — Gurpreet Kaur
(74) *Attorney, Agent, or Firm* — Baker Botts L.L.P.

(57) ABSTRACT

In an apparatus for analyzing small number of samples, wasteful consumption of a polymer as a separation Medium is suppressed.

The apparatus has a configuration provided with a plurality of capillary units each of which can be attached/detached to/from the apparatus, and performs analysis for capillaries after sealing of a polymer by attaching the capillaries by the number in accordance with the number of samples. Since analysis can be performed by using capillaries by the number identical with that of the samples to be analyzed, wasteful polymer is not used in the capillaries not used for the analysis. In addition, the polymer injection mechanism is unnecessary and the polymer is not necessary for maintenance and upon starting of analysis. An electrophoresis apparatus which is small in the size with no polymer injection mechanism, and with low running cost not wastefully consuming the polymer can be provided.

6 Claims, 6 Drawing Sheets

(58) Field of Classification Search
USPC .............................. 204/601, 605, 451, 455
See application file for complete search history.

(56) References Cited

U.S. PATENT DOCUMENTS

| | | | |
|---|---|---|---|
| 5,582,705 | A | 12/1996 | Yeung et al. |
| 5,605,666 | A | 2/1997 | Goodale et al. |
| 5,833,827 | A | 11/1998 | Anazawa et al. |
| 6,364,516 | B1 | 4/2002 | Li et al. |
| 2003/0062310 | A1* | 4/2003 | Zare ................ B01J 20/262 210/656 |
| 2005/0189219 | A1 | 9/2005 | Amirkhanian et al. |
| 2006/0186029 | A1* | 8/2006 | Granger ............. G01N 30/6069 210/198.2 |
| 2009/0020429 | A1* | 1/2009 | Ozawa ............. G01N 27/44708 204/604 |
| 2010/0005867 | A1* | 1/2010 | Doerr ................ B01L 3/5027 73/61.53 |
| 2010/0175996 | A1* | 7/2010 | Tanaka ............. G01N 27/44756 204/451 |
| 2010/0213112 | A1* | 8/2010 | Bischoff ................ B01D 15/22 210/198.2 |

FOREIGN PATENT DOCUMENTS

| | | |
|---|---|---|
| JP | 8-500188 | 1/1996 |
| JP | 11-211694 | 8/1999 |
| JP | 2000-88803 | 3/2000 |
| JP | 2000-137020 | 5/2000 |
| JP | 2003-524747 | 8/2003 |
| WO | WO 94/29713 A1 | 12/1994 |
| WO | WO 99/00664 A1 | 1/1999 |
| WO | WO 2009/067640 A2 | 5/2009 |
| WO | WO 2010/119805 | 10/2010 |

OTHER PUBLICATIONS

Extended European Search Report, dated Apr. 4, 2017, which issued during the prosecution of European Patent Application No. 11856763.5, which corresponds to the present application.

* cited by examiner

ENLARGED PORTION A 106

FIG. 4

ENLARGED PORTION B 116

FIG. 5

ENLARGED PORTION C 127

ELECTROPHORESIS APPARATUS, CAPILLARY ARRAY, AND CAPILLARY UNIT

TECHNICAL FIELD

The present invention relates to a technique of separating and analyzing nucleic acids, proteins, etc. by electrophoresis and it relates, for example, to a capillary electrophoresis apparatus.

BACKGROUND ART

An electrophoresis method using a capillary has been used for determining the base sequence and base length of DNA, etc.

One of light irradiation systems to a plurality of capillaries includes a multi-focus system described in Patent Literature 1. In this system, capillaries at one or both of the ends of a capillary array comprising a plurality of capillaries arranged on a plane substrate are irradiated with a laser light, the laser light crosses the capillary array while propagating adjacent capillaries successively, and emission of light generated at the capillary array is detected by a light detector. A sample containing DNA labeled by a fluorescent dye is introduced into the capillary and irradiated by the laser light so as to propagate a plurality of capillaries arranged in a row. Fluorescent dye-labeled DNA emits fluorescence by laser light irradiation of the capillaries. DNA of the sample introduced into each of the capillaries can be analyzed by measuring fluorescence from each of the capillaries. This is identical also in the analysis of proteins, etc.

CITATION LIST

Patent Literature

Patent Literature 1: U.S. Pat. No. 5,582,705

SUMMARY OF THE INVENTION

Technical Problem

As a result of an earnest study made by the present inventors, the following subjects have been found.

In the capillary array apparatus comprising a plurality of capillaries, since the plurality of capillaries are formed integrally, there is a problem that a polymer as a separation medium is consumed wastefully as shown below. For example, when four samples are measured in an electrophoresis apparatus having eight capillaries, while only the four capillaries are used, the polymer is injected also to other four capillaries. Thus, there is a problem that running cost increases.

On the other hand, in an apparatus having a pumping function for injecting the polymer to the capillary array, when the operation frequency is low such as once or twice operation per one week, since a great amount of the polymer is consumed for filling the flow channel in the pump with the polymer or for maintenance, there is a problem that the running cost increases or maintenance is always necessary for keeping the function.

Solution to Problem

The present invention provides a capillary array electrophoresis apparatus having a light emission transmission/detection system of applying an exciting light to a capillary at the end of a capillary array comprising a plurality of capillaries arranged on a plane, the exciting light propagating adjacent capillaries successively and crossing the capillary array, and focusing light emission generated in the capillary array over a light collection/light detection device, in which the capillaries are detachable each independently in a state being sealed with a separation medium to/from the electrophoresis apparatus, a capillary end on the side of a cathode of the apparatus is connected with resin members each apertured with a hole, a capillary end on the side of an anode of the apparatus is connected with resin members each apertured with a hole, and both of the cathode and anode sides are connected to the apparatus vertically to the surface of a buffer solution.

Further, the present invention provides an electrophoresis apparatus comprising a capillary array having a plurality of capillaries which are detachable each by one and not requiring a pumping function for re-packing a polymer.

Further, the capillaries detachable are each sealed with a polymer as a separation medium, stored in a state tightly closed at both ends and usable by detaching sealing on the side of the cathode for every use before attachment to the apparatus.

The present invention provides a capillary electrophoresis apparatus capable of selecting a capillary of an appropriate length and an appropriate separation medium for every sample when multiple different kinds of samples are analyzed simultaneously.

Advantageous Effects of Invention

In the electrophoresis apparatus in which capillaries at both ends of a capillary array comprising a plurality of capillaries arranged in a plane substrate are irradiated with a laser light, the laser light successively propagating to adjacent capillaries, the capillaries can be used by a necessary number in accordance with the number of samples. Further, a capillary containing a new separation medium can be mounted and analyzed for every use.

Since a re-packing pump for the polymer as the separation medium is not used, maintenance is not necessary.

DESCRIPTION OF EMBODIMENTS

The foregoing and other novel features and advantages of the present invention are described with reference to the drawings. However, the drawings are only for the purpose of illustration and not intended to define the scope of the invention.

First Embodiment

Figure 1:
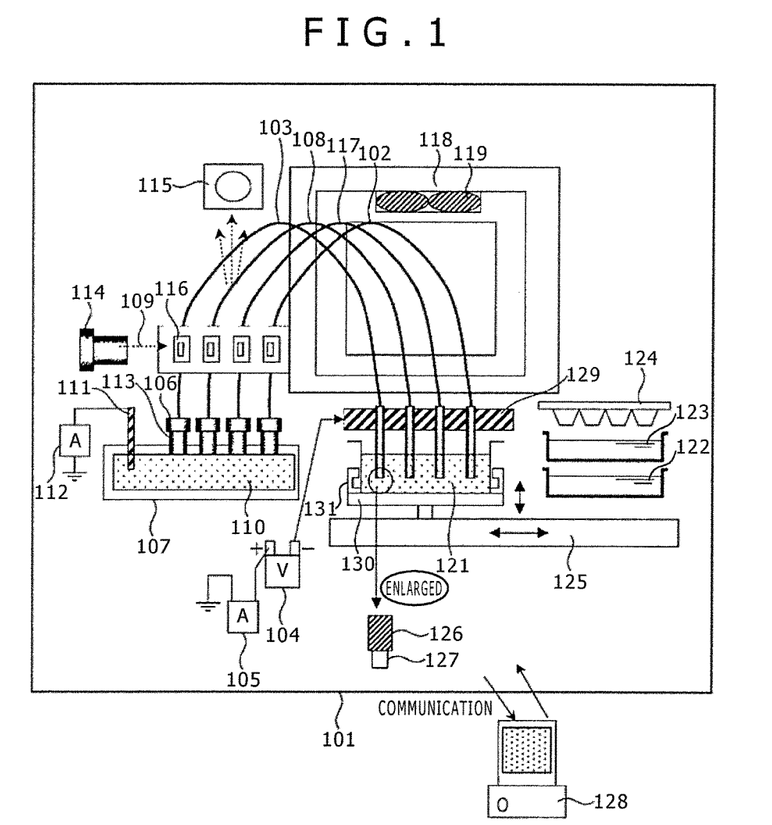
FIG. 1 is a schematic view of an electrophoresis apparatus according to this embodiment.

FIG. 1 is a schematic view of an electrophoresis apparatus according to this embodiment. The configuration of the apparatus is to be described with reference to FIG. 1.

The present apparatus comprises a detection portion 116 for optically detecting a sample, a thermostatic bath 118 for keeping the temperature of a capillary thermostatically, a transporting device 125 for transporting various vessels to the cathode end of the capillary, a high voltage power supply 104 for applying a high voltage to the capillary, a first current meter 105 for detecting a current generated from the high voltage power supply, a second current meter 112 for detecting a current flowing to the electrode on the side of the anode, and a capillary array 117 comprising one or a plurality of capillary units 103.

The capillary array 117 is an exchangeable member including a capillary 102 comprising four capillary units 103 which are detachable independently and coated with a polyimide, and includes a cathode end 127 of the capillary, a detection portion 116, and a capillary head as an anode end 106 of the capillary. When the measuring method is changed, the capillary array is replaced and the length of the capillary is adjusted. Further, when breakage or deterioration of quality is found in the capillary, it is replaced with a new capillary array.

The capillary comprises a glass tube having an inner diameter of several tens to several hundreds μm and an outer diameter of several hundred μm and coated at the surface with a polyimide for improving the strength. However, the light irradiation portion irradiated by a laser light has a structure in which the polyimide coating film is removed so that light emission in the inside tends to leak to the outside. A separation medium for providing a difference of a migration speed during electrophoresis is filled in the inside of the capillary 102. The separation medium includes both of flowable and non-flowable media and a flowable polymer is used in this example.

The detection portion 116 is a member for obtaining information depending on a sample, which is irradiated with an exciting light and emits light at a wavelength depending on the sample. The detection portions of respective four capillaries are attached to an attaching portion 108 of the capillary detection portion and arranged and fixed near the light irradiation portion on the optically flat surface at an accuracy of several μm height.

An irradiation detection portion of the optical system comprises a light source 114 for irradiating the detection portion 116, and a light detector 115 for detecting light emission in the detection portion 116. During electrophoresis, a laser light 109 is applied and continuously passes through all of the light irradiation portions. By the laser light, information light (fluorescence having a wavelength depending on the sample) is generated from the sample and emitted from the light irradiation portion to the outside. The information light is detected by the light detector 115 and the sample is analyzed. The laser light is applied to all of the capillary detection portions fixed to of the capillary detection portion of the capillary detection portion an attaching portion 108 of the capillary detection portion, and the light detector detects the fluorescence generated from all of the capillaries.

The cathode ends 127 of the capillary are respectively passed through and fixed respectively in hollow electrodes 126 made of metal and the top end of the capillary is protruded by about 0.5 mm from the hollow electrode 126. Further, the hollow electrodes 126 provided for every capillary are mounted together with the capillary units 103 to a load header 129 appended to the apparatus. Further, all of the hollow electrodes 126 are in electric conduction with the high voltage power supply 104 mounted to the apparatus main body by way of the load header 129 and operate as a cathode electrode when it is necessary to apply a voltage, for example, during electrophoresis or upon introduction of the sample.

The anode end 106 of the capillary on the side opposite to the cathode end 127 of the capillary can be connected airtightly to a block 107. Then, an anode buffer 110 fills the inside of the block 107 and the anode end 106 of the capillary is connected by way of the capillary head connection part 113 to the anode buffer. A plurality of capillary head connection part are provided in the block 107, connected for every capillary and dipped in the anode buffer, thereby operating as the anode electrode.

A thermostatic bath 118 is covered with a heat insulating material in order to keep the inside of the thermostatic bath at a constant temperature and controlled for the temperature by a heating and cooling mechanism. Further, a blower 119 circulates and stirs air in the thermostatic bath and keeps the temperature of the capillary array 117 positionally uniform and constant.

A conveying device 125 has three electric motors and linear actuators and is movable along three axes, that is, vertically, horizontally, and in the direction of the depth. Further, at least one vessel can be placed over a moving stage 130 of the conveying device 125. Further, an electromotive grip 131 is provided to the moving stage 130 and can catch or release each of the vessels. Accordingly, a buffer vessel 121, a cleaning vessel 122, a liquid waste vessel 123, and a sample vessel 124 can be conveyed optionally to the cathode end. Unnecessary vessels are stored in a predetermined storing place in the apparatus.

The apparatus main body 101 is used in a state connected by way of a communication cable with a controlling computer 128. By the controlling computer 128, an operator can control the function of the apparatus and can transmit and receive data detected by the detector in the apparatus.

Figure 2:
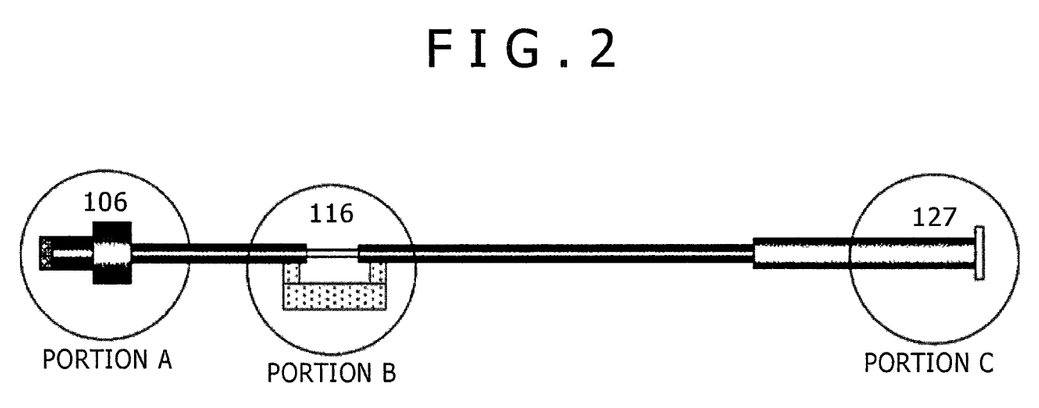
FIG. 2 is a schematic view of a capillary unit as a first embodiment of the present invention.

A schematic view of the capillary unit of this apparatus is illustrated in FIG. 2 and an example is to be described.

As illustrated in FIG. 2, the capillary unit comprises one capillary and has an anode end 106 of the capillary, a detection portion 116, and a cathode end 127 of the capillary. A polymer as a separation medium is sealed in the capillary.

Figure 3:
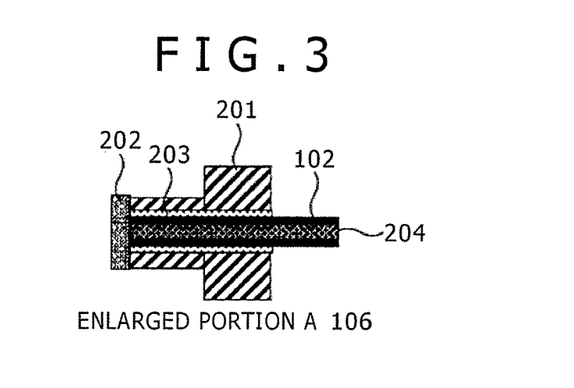
FIG. 3 is an enlarged view for a portion A in FIG. 2.

FIG. 3 illustrates a detailed cross section at the anode end of the capillary. The capillary is fixed to a capillary head 201 by using an adhesive 203. The capillary head comprises an insulating resin material. A polymer 204 as a separation membrane is preliminarily injected in the capillary and sealed with an anode sealing material 202. Accordingly, while it is not in contact with external air during storage of the capillary, the anode sealing material comprises an electroconductive material to ensure electric conduction with the outside. Accordingly, when the capillary is immersed in the anode buffer, electric conduction can be established between the anode electrode and the polymer inside the capillary. That is, electrophoresis can be carried out with no involvement of bubbles in the capillary with the polymer being fixed as it is. The material for the anode sealing member comprises an electroconductive resin which is preferably stable under a high voltage.

The anode sealing member can also be detached before use and the apparatus per se can perform electrophoresis with the capillary head being connected directly to the block 107 on the side of the apparatus.

Figure 4:
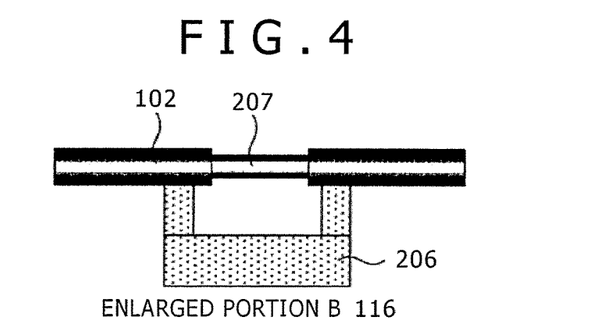
FIG. 4 is an enlarged view for a portion B in FIG. 2.

FIG. 4 illustrates a detection portion 116 of the capillary unit. The capillary comprises a quartz glass tube coated with a thin polymer film in which the polymer coating film is removed at the detection portion to expose a quartz part. The inner diameter/outer diameter of the quartz tube is 50/320 µm and the outer diameter of the capillary including the thin polymer film is 363 µm. The capillary is fixed to a reference base 206 in a state of protecting a coating-removed portion 207. The detection portion of each capillary is attached to an attaching portion 108 of the detection portion with the reference base as an attaching reference to constitute a detection portion comprising a plurality of capillaries. Details are illustrated in FIG. 8.

Figure 5:
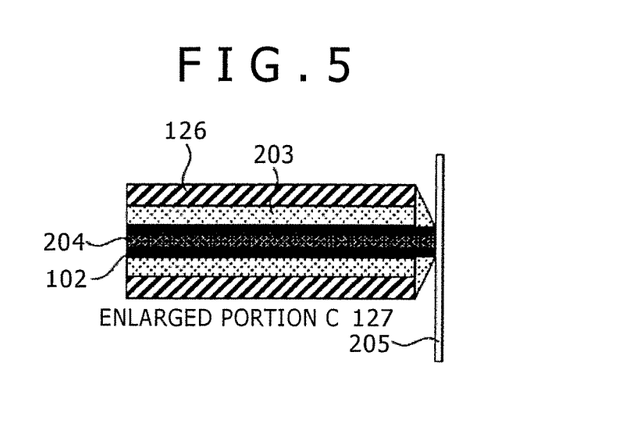
FIG. 5 is an enlarged view for a portion C in FIG. 2.

FIG. 5 illustrates a cross sectional view of a cathode end of the capillary. The capillary is fixed to a hollow electrode 126 by using an adhesive 203. A polymer 204 as a separation medium is preliminarily injected into the capillary, and sealed with a cathode sealing member 205 during storage of the capillary unit, so that it is not in contact with external air during storage of the capillary. The cathode sealing member is detached upon mounting of the capillary to the apparatus, that is, before analysis.

Figure 6:
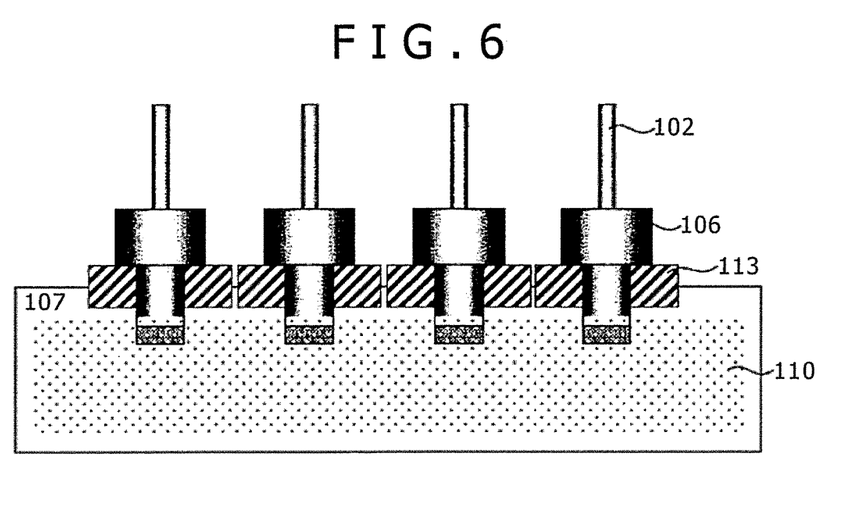
FIG. 6 is a schematic view on the side of an anode of a capillary as the first embodiment of the present invention.
Figure 7:
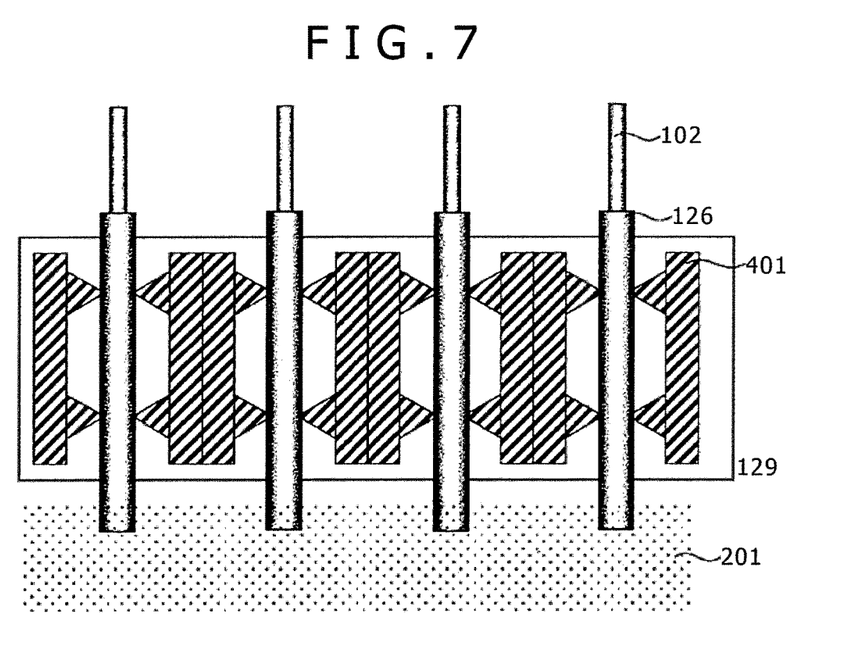
FIG. 7 is a schematic view on the side of a cathode of the capillary as the first embodiment of the present invention.
Figure 8:
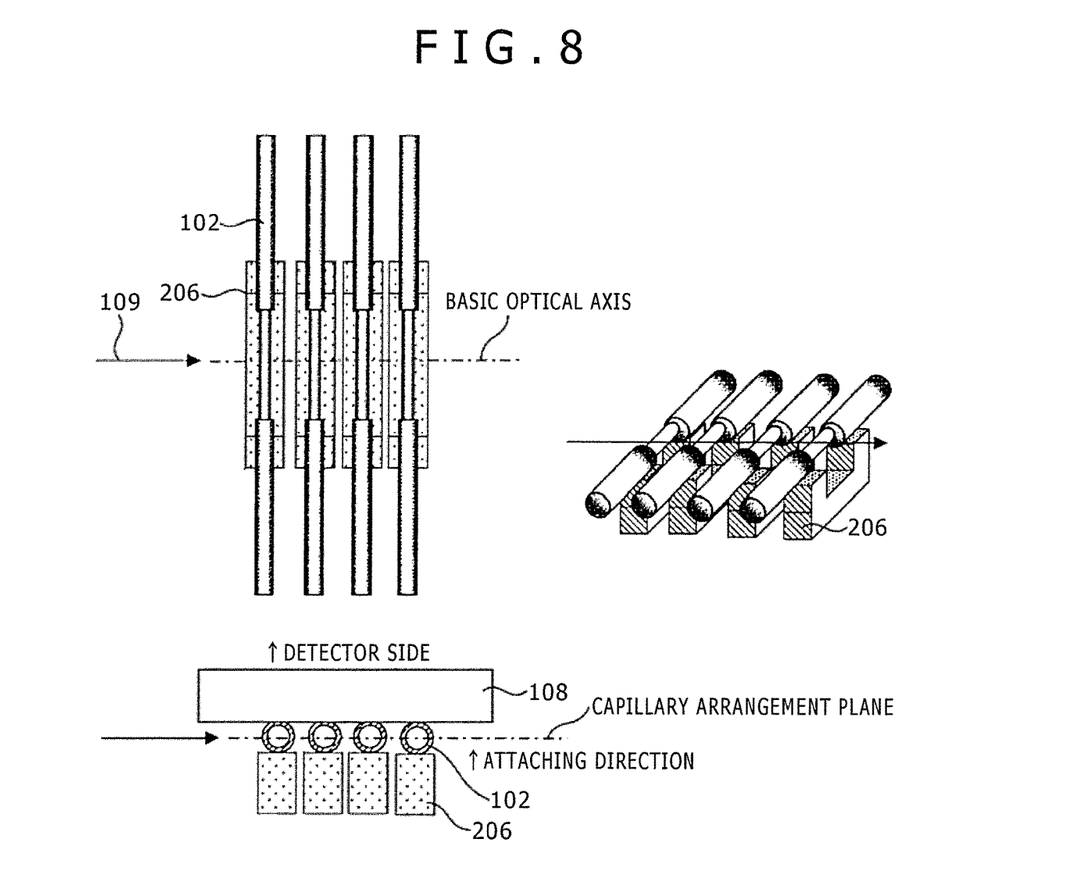
FIG. 8 is a schematic view of an irradiation detection portion of a multi-capillary as the first embodiment according to the present invention.

Then, a method of mounting the capillary unit to the apparatus and the method of fluorescence detection are to be shown with reference to FIGS. 6 to 8.

FIG. 6 illustrates connection on the side of the anode of the capillary unit. A block 107 containing an anode buffer 110 is attached on the side of the anode to the apparatus. The anode buffer 110 is connected by way of electrode 111 to the ground. The anode buffer 110 is replaceable and can be replaced optionally by a user. Capillary head connection portions 113 are attached by the number identical with that of connectable capillaries to the block 107. The capillary head connection portions 113 are made of a high voltage withstanding resin material and each formed with a hole having a diameter substantially identical with the diameter of the capillary head, and the capillary head is fixed to the block by utilizing the hole. Further, the capillary head is dipped through the hole in the anode buffer to ensure electric conduction between each of the polymer inside the capillary, the solution buffer, and the ground.

FIG. 7 illustrates connection of the capillary units on the side of the cathode. On the side of the cathode, a load header 129 for connecting and fixing the hollow electrodes 126 is attached to the apparatus. In the load header 129, cathode connectors 401 by the number identical with that of the connectable capillaries are incorporated for fixing the hollow electrodes 126. The hollow electrode of each of the capillary units is in contact at two points with of cathode connector and the hollow electrodes are mounted vertically to the load header 129 appended to the apparatus. Further, since the cathode connector is in electric conduction with the high voltage power supply 104, all of the hollow electrodes 126 are in electric conduction by way of the load header to the high voltage power supply 104 mounted on the apparatus main body. The hollow electrode 126 operates as the cathode electrode when it is necessary to apply a voltage, for example, during electrophoresis or upon sample introduction.

FIG. 8 illustrates a method of attaching the detection portion of the capillary unit and irradiation and detection of exciting light for a plurality of the capillaries. In the capillary unit, the capillaries are fixed being arranged over reference bases 206. Respective independent capillary units are arranged over an attaching portion 108 of the capillary detection portion with the attaching surface being as a reference, to form an array of a plurality of capillary.

A plane defined by central axes of four capillaries over the capillary detection portion attaching portion and a imaginary plane defined by extending the plane for the entire space are referred to as a capillary arrangement plane. Further, an imaginary straight line over the capillary arrangement plane, perpendicular to the four capillary axes and passing through the center of the detection portion is hereinafter referred to as a basic optical axis. A laser light 109 introduced from one side of the capillary array is in parallel to the capillary arrangement plane and coaxial with the basic optical axis.

DNA is detected by applying a laser light 109 from one lateral side of the array to the fluorescence detection portion in the capillary array and observing the fluorescence emitted from the detection portion. A capillary situated at the end of the array and introduced with the laser light is hereinafter referred to as a first capillary. The laser light introduced to the first capillary propagates to adjacent capillaries successively and crosses the four capillaries. The intensity of the laser light is not decayed so much when the number of the capillaries is about four and the light propagates as far as the capillary on the side opposite to the first capillary and a similar intensity of fluorescence detection can be obtained for all of the four capillaries.

The performance obtained according to the present invention is to be described.

As the advantageous effect of the invention, 1) since analysis can be performed by using capillaries by the number identical with the number of the samples to be analyzed, use of a wasteful polymer for the capillary not used for the analysis can be avoided, and 2) a polymer injection mechanism is unnecessary and the polymer is not necessary for maintenance or upon starting of analysis.

In view of the above, an electrophoresis apparatus not requiring the polymer injection mechanism and not wastefully consuming the polymer can be provided.

Second Embodiment

Figure 9:
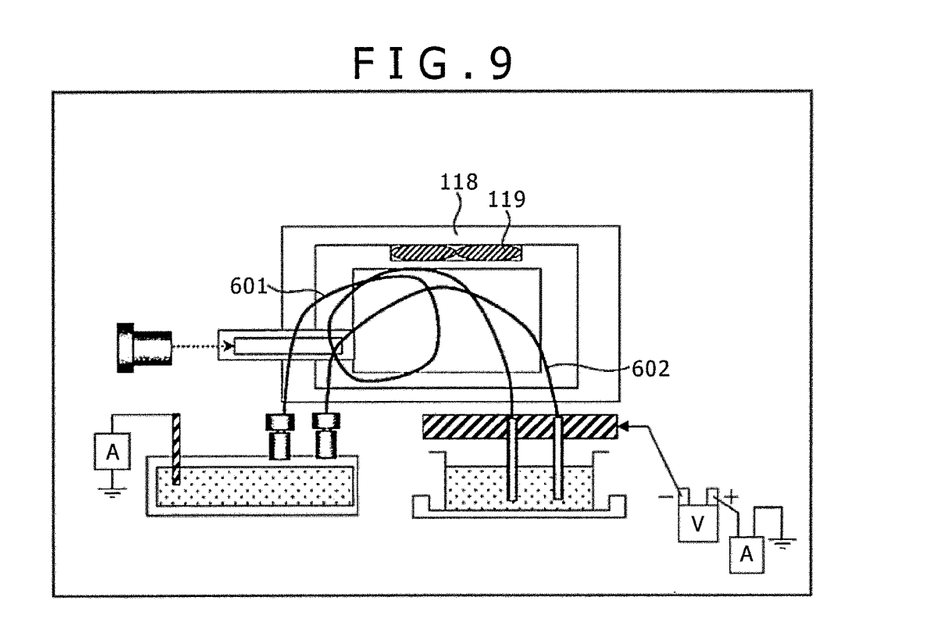
FIG. 9 is a schematic view of an electrophoresis apparatus upon mounting capillaries of different lengths in a second embodiment of the present invention.

A second embodiment is to be described. FIG. 9 illustrates a schematic view of a capillary array of the second embodiment and apparatus of the invention.

In the first embodiment, the electrophoresis apparatus using a capillary array comprising a plurality of the same kind of capillary units has been described. In this embodiment, description is to be made to an example of using a capillary array comprising different kinds of capillary units. Different kinds indicate a capillary unit having different capillary lengths or a capillary unit in which different kinds of separation media are sealed. In this example, a capillary unit 601 of 50 cm length and a capillary unit 602 of 36 cm unit are connected simultaneously to the apparatus. In this example, the capillary of 50 cm capillary unit is arranged such that the planar area is substantially identical between the 50 cm capillary unit and the 36 cm capillary unit. Accordingly, there is no requirement of enlarging the size of the thermostatic bath and the size of the entire apparatus can be decreased.

By mounting the capillary units of different lengths, analysis suitable to respective samples can be performed simultaneously for each of the samples. The operation time of the apparatus, consumption products, etc. can be saved.

Further, by analyzing an identical sample by using separate capillary units, bases of longer length can be analyzed. That is, 1200 bases in total can be analyzed at a time by analyzing a short portion of 10 to 600 bases in a short capillary unit and a long portion of 400 to 1200 bases in a long capillary unit.

Third Embodiment

Figure 10:
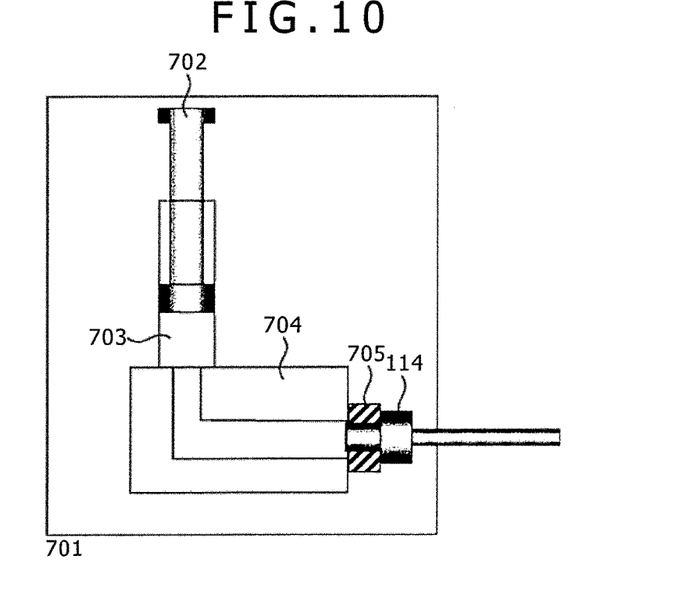
FIG. 10 is a schematic view of an external polymer re-packing mechanism according to a third embodiment of the present invention.

A third embodiment is to be described. FIG. 10 illustrates a schematic view for an external polymer injection mechanism and a capillary head portion of a capillary unit in the third embodiment.

Description has been made for the first embodiment that a capillary unit in the state of storage in which the polymer as the separation medium is preliminarily sealed is connected to the apparatus and used. In this embodiment an external polymer injection mechanism for replacing the separation medium in a capillary unit for which analysis has been once completed is illustrated.

A polymer injection mechanism 701 illustrated in FIG. 10 comprises a syringe 702, a polymer block 704, and a capillary connection portion 705. A new polymer is filled in the syringe and the polymer block, and the polymer injection mechanism can always be preserved in a cold state. Upon use, the polymer injection mechanism is taken out of a refrigerator, connected to a capillary unit which has been used and detached from the apparatus, and the polymer is replaced. Upon connection of the capillary unit, a capillary connection portion 705 and the capillary head of the capillary unit are connected.

The capillary unit can be used repetitively, wasteful loss upon replacement of the polymer is avoided, and the polymer can be stored in a fresh state for a long time.

Embodiments of the present invention have been explained above but persons skilled in the art will understood that the present invention is not restricted to them but can be modified variously within the range of the invention described in the scope of the claim for patent. Appropriate combination of each of the embodiments is also within the range of the invention.

LIST OF REFERENCE SIGNS

101 apparatus main body
102 capillary
103 capillary unit
104 high voltage power supply
105 first current meter
106 anode end of capillary
107 block
108 attaching portion of capillary detection portion
109 laser light
110 anode buffer
111 electrode (GND)
112 second current meter
113 capillary head connection portion
114 light source
115 light detector
116 detection portion
117 capillary array
118 thermostatic bath
119 blower
121 buffer vessel
122 cleaning vessel
123 liquid waste vessel
124 sample plate
125 conveying device
126 hollow electrode
127 cathode end of capillary
128 controlling computer
129 load header
130 moving stage
201 capillary head
202 anode sealing material
203 adhesive
204 polymer
205 cathode sealing material
206 reference base
207 coating-removed portion
401 anode connector
601 50 cm capillary unit
602 36 cm capillary unit
701 polymer injection mechanism
702 syringe
703 polymer in the syringe
704 polymer block
705 capillary connection portion

The invention claimed is:

1. A capillary unit including:
   a capillary comprising a tube filled with a separation medium in the inside and coated at the outer side at least excluding a portion,
   an anode sealing member and a cathode sealing member disposed proximate to opposing ends of the tube and forming an airtight seal proximate the opposing ends, wherein the anode sealing member comprises an electroconductive material and wherein the cathode sealing member is configured to be detached from the tube prior to use, and
   wherein the anode sealing member comprises a capillary head fixed to the capillary by an adhesive.

2. The capillary unit according to claim 1, wherein a hollow electroconductive pipe is provided on one end of the capillary and a top end of the capillary protrudes out of the hollow pipe.

3. The capillary unit according to claim 1, wherein the anode sealing member and the cathode sealing member each defines an exterior surface of the capillary unit.

4. The capillary unit according to claim 1, wherein at least one of the anode sealing member or the cathode sealing member defines an exterior surface of the capillary unit.

5. The capillary unit according to claim 1, wherein the separation medium comprises a polymeric material.

6. The capillary unit according to claim 1, wherein the separation medium comprises a fluid medium extending the length of the tube to each of the opposing ends.

* * * * *